(12) United States Patent
Bowen

(10) Patent No.: US 6,790,039 B1
(45) Date of Patent: Sep. 14, 2004

(54) DENTAL TURBINE SUPPORT STRUCTURE

(75) Inventor: Stanley A. Bowen, Santa Ana, CA (US)

(73) Assignee: Dental EZ, Inc., Wynnewood, PA (US)

( * ) Notice: Subject to any disclaimer, the term of this patent is extended or adjusted under 35 U.S.C. 154(b) by 0 days.

(21) Appl. No.: 10/453,301

(22) Filed: Jun. 2, 2003

(51) Int. Cl.$^7$ ................................................. A61C 1/05
(52) U.S. Cl. ..................................................... 433/132
(58) Field of Search ................................ 433/132, 131, 433/133, 126, 114

(56) References Cited

U.S. PATENT DOCUMENTS

| | | |
|---|---|---|
| 4,249,896 A | 2/1981 | Kerfoot, Jr. |
| 5,022,857 A | 6/1991 | Matsutani et al. |
| 5,286,065 A | 2/1994 | Austin et al. |
| 5,496,173 A | 3/1996 | Wohlgemuth |
| 5,507,642 A | 4/1996 | Wohlgemuth |
| 5,676,542 A * | 10/1997 | Lingenhole et al. ........ 433/115 |
| 5,733,120 A | 3/1998 | Yao et al. |
| 5,779,474 A * | 7/1998 | Gonser ........................ 433/129 |
| 5,795,167 A | 8/1998 | Brenner |
| 5,938,441 A | 8/1999 | Brenner |
| 6,250,921 B1 | 6/2001 | Esrock |
| 6,315,560 B1 | 11/2001 | Krouglicof et al. |

* cited by examiner

*Primary Examiner*—Kevin Shaver
*Assistant Examiner*—Melba Bumgarner
(74) *Attorney, Agent, or Firm*—Akin Gump Strauss Hauer & Feld, LLP

(57) ABSTRACT

A support structure for a turbine motor for use in a dental handpiece includes a pair of resilient rings to capture and limit rotation of an outer race of a bearing supporting a rotor of the turbine motor. The turbine motor is supported by first and second bearing assemblies, the first bearing assembly being proximate a dental tool and the second bearing assembly being distal the dental tool. The pair of rings are preferably located on the first bearing assembly, but optionally could be located on only the second bearing assembly or on both first and second bearing assemblies. The support structure further includes a resilient spacer ring located on the second bearing assembly to provide axial pre-load to the bearing assemblies.

6 Claims, 3 Drawing Sheets

DENTAL TURBINE SUPPORT STRUCTURE

BACKGROUND OF THE INVENTION

The present invention relates to high-speed turbine motors used in dental handpieces. In particular, the invention relates to the manner in which dental turbines are supported within the dental handpieces.

Dental handpieces having gas-driven turbine motors are well known. Of particular interest herein is a high-speed gas-driven dental handpiece having decreased noise and improved vibration damping characteristics.

U.S. Pat. No. 4,249,896 to Kerfoot, Jr. discloses a dental handpiece having a high-speed gas-driven turbine motor. A dental turbine motor of this type will rotate at speeds of over 400,000 rpm during use of the handpiece by a dentist. At such extreme speeds, minor imbalances may cause significant vibration and noise, which may impair the function and durability of the turbine and create discomfort and distractions to both dentist and patient. A support structure which provides noise and vibration damping to the turbine motor is thus desirable.

It is well-known in the art to provide first and second bearing assemblies to rotatably support a turbine motor within a dental handpiece, the first bearing being proximate a dental tool and the second bearing being distal the dental tool. From the Kerfoot, Jr. patent, it is further known to provide a single resilient ring, such as an o-ring made from a material such as neoprene, to capture an outer race of such bearings. The resilient ring provides radial support for the turbine motor assembly within the housing of the handpiece and substantially dampens the transfer of vibration from the motor assembly to the handpiece during use of the handpiece. Kerfoot, Jr. further discloses that a turbine motor assembly may include a spring washer which may be used to provide axial pre-load into the turbine motor bearing assemblies to further improve the dynamic characteristics of the device. More particularly, Kerfoot, Jr. discloses a single spring washer located at the first bearing assembly or first and second spring washers located at the first and second bearing assemblies, respectively. Kerfoot, Jr. does not disclose a single spring washer located only at the second bearing assembly.

A problem associated with the prior art, particularly the design disclosed in Kerfoot, Jr., is the difficulty in providing a method of supporting the outer race of a bearing assembly such that the outer race is prevented from spinning when the rotor and inner race are rotating. Spinning of the outer race of the bearing is detrimental to bearing life. A second problem associated with the prior art, again particularly the Kerfoot, Jr. design, is that a spring washer provided at the first bearing assembly proximate to the dental tool tends to experience excessive deflections, deform and flatten with use, lose the capability of providing axial pre-load and require frequent replacement.

There is need, therefore, for a high-speed gas-driven dental turbine having support structure which improves durability of the bearing assemblies while also adequately attenuating vibration of the rotor. There is a further need for a dental turbine having support structure which improves durability of support structure elements providing axial pre-load to the bearing assemblies.

BRIEF SUMMARY OF THE INVENTION

According to one aspect of the invention, a dental handpiece for rotating a dental workpiece comprises a housing having a first end and a second end and a gas-driven turbine motor assembly including a rotor shaft having an axis of rotation substantially coincident with a central longitudinal axis of the housing. A chuck assembly secured to the rotor shaft, the chuck assembly releasably holding a shaft of the dental workpiece.

A first bearing assembly radially supports the motor assembly and is disposed toward the first end of the housing. The first bearing assembly includes:

an inner race fixed to the rotor shaft;

an outer race having an outer wall facing radially outwardly of the axis of the rotor shaft;

a plurality of movable bearing elements confined between the inner race and the outer race;

a first flange connected to a first end of the outer wall of the outer race, the first flange having a first lateral face disposed toward the first end of the housing and a second lateral face disposed toward the second end of the housing;

a first groove extending circumferentially about a second end of the outer wall of the outer race, the first groove lying in a plane substantially perpendicular to the axis of the rotor shaft;

a first snap ring retained within the first groove, the snap ring forming an annular-shaped collar extending radially outwardly of the outer race outer wall, the snap ring having first and second lateral faces, the first lateral face being oriented toward the first end of the housing and a portion of the first lateral face of the snap ring contacting a portion of the housing;

a first pair of resilient rings disposed between the second lateral face of the snap ring and the first lateral face of the flange and frictionally engaged with the outer wall of the outer race, each of the rings having an outer diameter sufficient to provide a compression fit between the outer wall of the outer race and the housing.

A second bearing assembly radially supports the motor assembly and is disposed toward the second end of the housing. The second bearing assembly includes:

an inner race fixed to the rotor shaft, an outer race having an outer wall facing radially outwardly of the axis of the rotor shaft;

a plurality of movable bearing elements confined between the inner race and the outer race;

a second flange connected to a first end of the outer wall of the outer race of the second bearing assembly, the second flange having a first lateral face disposed toward the first end of the housing and a second lateral face disposed toward the second end of the housing;

a second groove extending circumferentially about a second end of the outer race outer wall of the second bearing assembly, the second groove lying in a plane substantially perpendicular to the axis of the rotor shaft;

a second snap ring retained within the second groove, the second snap ring forming an annular-shaped collar extending radially outwardly of the outer race outer wall of the second bearing assembly, the second snap ring having first and second lateral faces, the second lateral face being oriented toward the second end of the housing and a portion of the second lateral face of the second snap ring contacting the housing;

a single resilient ring disposed between the first lateral face of the second snap ring and the second lateral face of the second flange and frictionally engaged with the outer wall of the outer race of the second bearing assembly, the ring having an outer diameter sufficient to provide a compression fit between the outer race outer wall and the housing;

a substantially flat washer disposed between the ring and the second lateral face of the second flange;

a resilient spring-like spacer ring interposed between the second face of the second flange and the flat washer, the spacer ring transmitting a controlled compression force between the outer race of the second bearing assembly and the housing to provide axial pre-loading of the first and second bearing assemblies.

BRIEF DESCRIPTION OF THE SEVERAL VIEWS OF THE DRAWINGS

The foregoing summary as well as the following detailed description of a preferred embodiment of the invention will be better understood when read in conjunction with the appended drawings. For the purpose of illustrating the invention, there is shown in the drawings an embodiment which is presently preferred. It should be understood, however, that the invention is not limited to the precise arrangements and instrumentalities shown.

In the drawings.

DETAILED DESCRIPTION OF THE INVENTION

Figure 1:
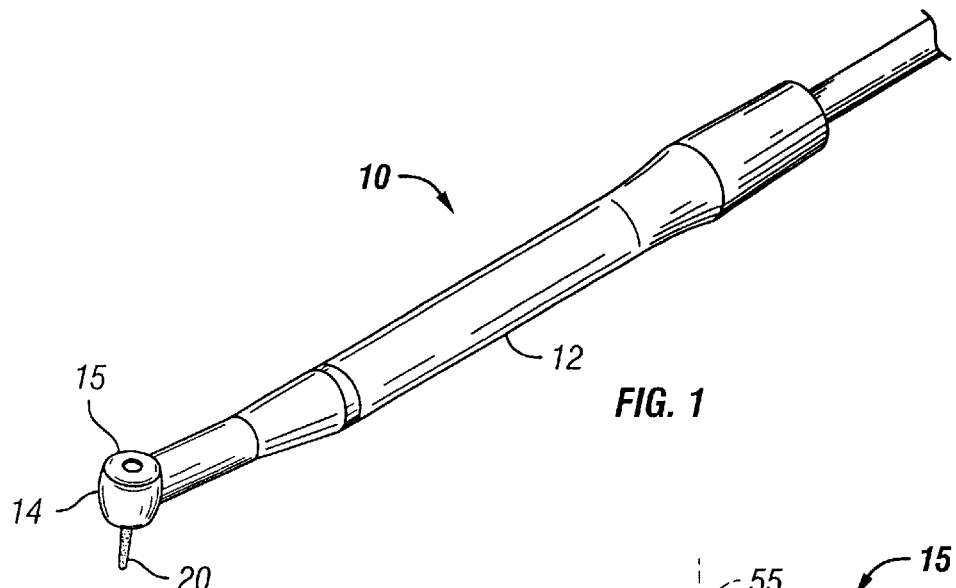
FIG. 1 is an upper front perspective view of a typical dental handpiece into which the turbine support structure of the present invention would be installed.

Certain terminology is used in the following description for convenience only and is not limiting. The words "lower" and "upper" designate directions in the drawings to which reference is made. The words "inwardly" and "outwardly" refer to directions toward and away from, respectively, the geometric center of the dental turbine and designated parts thereof. The word "a" is defined to mean "at least one". The terminology includes the words above specifically mentioned, derivatives thereof and words of similar import. In the drawings, like numerals are used to indicate like elements throughout.

Referring to the drawings, a preferred embodiment of the dental turbine support structure for a dental handpiece 10 of the present invention is disclosed. The dental handpiece 10 includes an elongated tubular housing 12 which terminates at a first end 14 in a turbine head 15. FIG. 1 illustrates a drill burr 20 installed into the turbine head 15. It will be appreciated that other dental workpieces can be installed into the turbine head 15.

Figure 2:
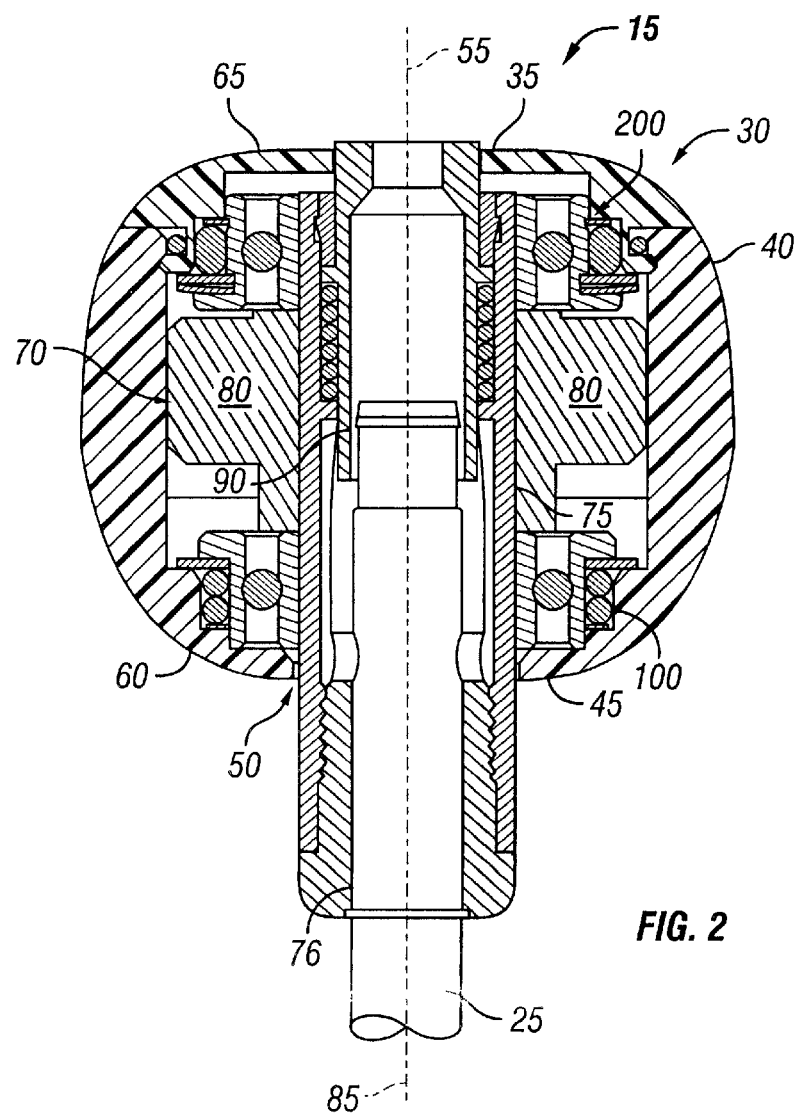
FIG. 2 is a side elevation view in cross-section of a dental turbine head, such as that illustrated in FIG. 1, showing the dental turbine support structure of the present invention.

Referring to FIG. 2, the turbine head 15 is shown in a side elevation cross-sectional view. The turbine head 15 is shown to include a turbine head housing 30. A generally flat turbine head endcap 35 removably attaches to the housing 30. The housing 30 further includes a generally cylindrical housing side wall 40 and a generally flat housing end wall 45. A centrally-located opening 50 is provided in the housing end wall 45. The end wall 45 is proximate a first end 60 of the turbine housing 30. The endcap 35 is proximate a second end 65 of the turbine housing 30. The housing 30 has a central longitudinal axis 55.

FIG. 2 further illustrates a turbine motor assembly 70. Major elements of the turbine motor assembly 70 include a turbine rotor shaft 75, turbine vanes 80, a chuck assembly 90, a first bearing assembly 100 disposed toward the first end 60 of the housing 30 and a second bearing assembly 200 disposed toward the second end 65 of the housing 30. The first and second bearing assemblies 100, 200 rotatably support the turbine rotor shaft 75. The turbine motor assembly 70 rotates about an axis of rotation 85 which is generally coincident with the turbine housing longitudinal axis 55. A shaft 25 of a dental workpiece, for example the dental burr 20, is inserted within a central cavity 76 of the rotor shaft 75, and held releaseably immobile relative to the rotor shaft 75 by the chuck assembly 90.

Figure 3:
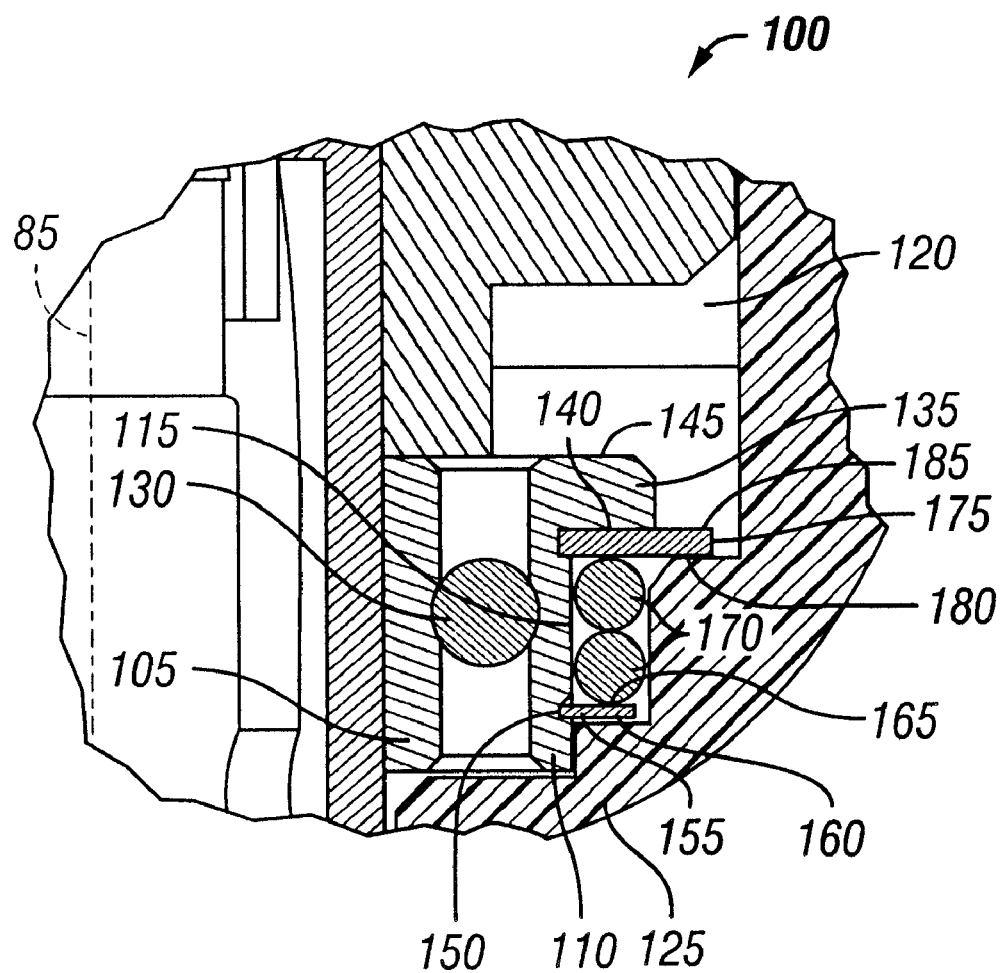
FIG. 3 is an enlarged detail view of a first bearing assembly of the dental turbine support structure of FIG. 2.

Now with particular reference to FIG. 3, the first bearing assembly 100 is shown in an enlarged detailed view. The first bearing assembly 100 includes a first annular inner race 105 fixed to the rotor shaft 75 and a first annular outer race 110. A first set of bearing elements 130 are disposed and confined between and are in frictional engagement with the first inner race 105 and the first outer race 110. The first outer race 110 includes a first outer wall 115 facing radially outwardly of the axis of rotation 85. The first outer wall 115 has a first end 120 and a second end 125. At the first end 120 of the first outer wall 115, a first flange 135 extends from the first outer wall 115. The first flange 135 has a first lateral face 140 disposed toward the first end 60 of the housing 30 and a second lateral face 145 disposed toward the second end 65 of the housing 30.

With continued reference to FIG. 3, a first groove 150 runs circumferentially about the second end 125 of the first outer wall 115. The first groove 150 lies in a plane substantially perpendicular to the axis of rotation 85. A first snap ring 155 is retained within the first groove 150, the first snap ring 155 forming an annular-shaped collar extending radially outwardly of the first outer wall 115. The first snap ring 155 has first and second lateral faces, 160 and 165, the first lateral face 160 being oriented toward the housing first end 60. A portion of the first snap ring first lateral face 160 contacts a portion of the housing sidewall 40.

A pair of rings 170 fabricated from a resilient material are disposed between the second lateral face 165 of the first snap ring 155 and the first lateral face 140 of the first flange 135. In a preferred embodiment, the pair of rings 170 are o-rings fabricated from Viton®. It would be obvious from this disclosure that rings with a non-circular cross-section and/or fabricated from other resilient materials, such as silicone, nitrite, or neoprene, could be substituted. The pair of rings 170 are frictionally engaged about a circumferential portion of the first outer wall 115, and each of the pair of rings 170 has an outer diameter sufficient to provide a compression fit between the first outer wall 115 and a portion of the housing side wall 40.

A substantially flat first washer 175 is disposed between the pair of rings 170 and the first lateral face 140 of the first flange 135. The first washer 175 has an outer diameter extending beyond an outer diameter of the first flange 135 and outer diameters of each of the pair of rings 170. The first washer 175 also has a first lateral face 180 oriented toward the housing first end 60. An outer portion of the first lateral face 180 of the first washer 135 contacts a portion of the housing side wall 40.

Figure 4:
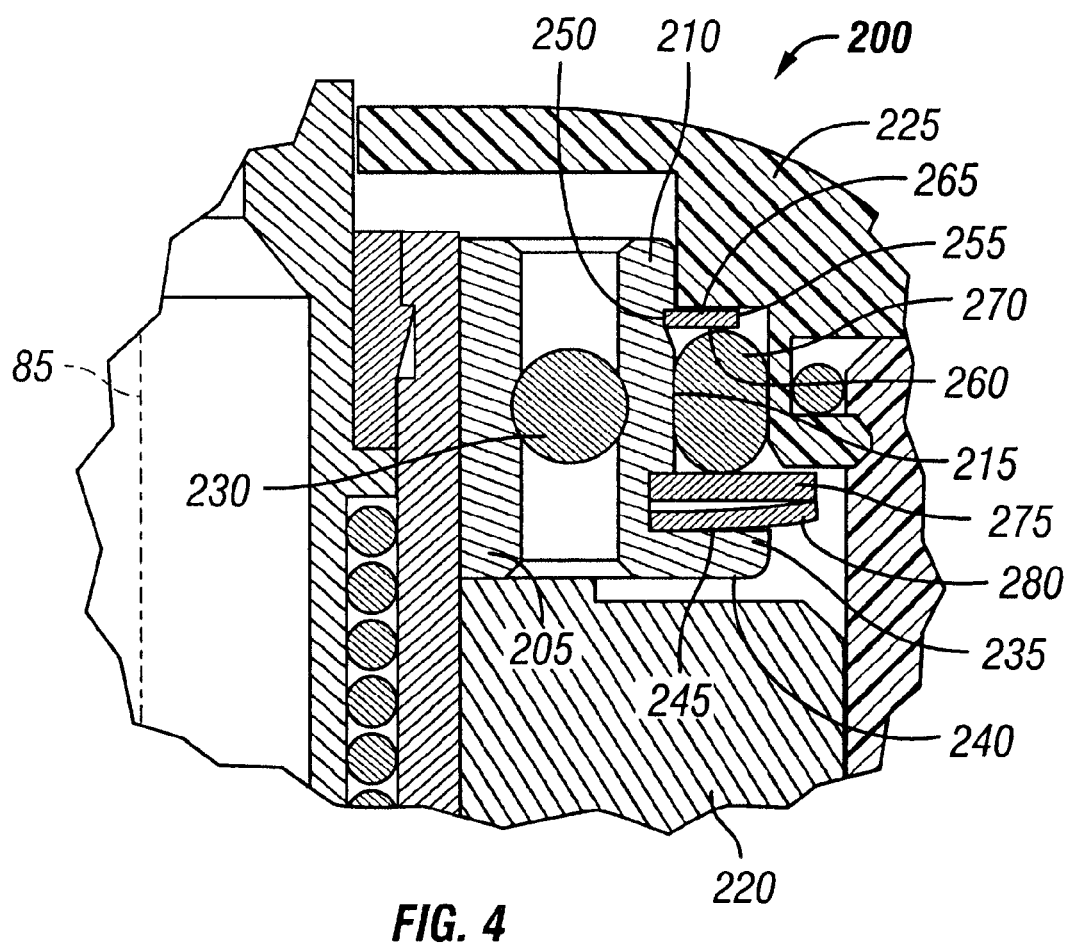
FIG. 4 is an exlarged detail view of a second bearing assembly of the dental turbine support structure of FIG. 2.

Now with particular reference to FIG. 4, the second bearing assembly 200 is shown in an enlarged detailed view. The second bearing assembly 200 includes a second annular inner race 205 fixed to the rotor shaft 75 and a second annular outer race 210 having a second outer wall 215 facing radially outwardly of the axis of rotation 85. A second set of movable bearing elements 230 are disposed and confined between and are in frictional engagement with the second inner race 205 and the second outer race 210. The second outer wall 215 has a first end 220 and a second end 225. A second flange 235 is connected to the first end 220 of the second outer wall 215. The second flange 235 has a first lateral face 240 disposed toward the first end 60 of the housing 30 and a second lateral face 245 disposed toward the second end 65 of the housing 30.

A second groove 250 runs circumferentially about the second end 225 of the second outer wall 215, the second groove 250 lying in a plane substantially perpendicular to the axis of rotation 85. A second snap ring 255 is retained within the second groove 250, the second snap ring 250 forming an annular-shaped collar extending radially outwardly of the second outer wall 215. The second snap ring 255 has first and second lateral faces, 260, 265, the second lateral face 265 being oriented toward the second end 65 of the housing 30 and a portion of the second lateral face 265 of the second snap ring 255 contacting a portion of the endcap 35.

A single ring 270 of resilient material is disposed between the first lateral face 260 of the second snap ring 255 and the second lateral face 245 of the second flange 235. The single ring 270 is an o-ring preferably fabricated from a natural or synthetic rubber or rubber-like material, for example, Viton®. It would be obvious from this disclosure that rings with a non-circular cross-section and/or fabricated from other resilient materials, such as silicone, nitrile, or neoprene, could be substituted. The single ring 270 is frictionally engaged about a circumferential portion of the second outer wall 215, and the single ring 270 has an outer diameter sufficient to provide a compression fit between the second outer wall 215 and a portion of the housing end cap 35.

A substantially flat second washer 275 is disposed between the single ring 270 and the second lateral face 245 of the second flange 235. A resilient spacer ring 280 is interposed between the second lateral face 245 of the second flange 235 and the second washer 275. The spacer ring 280 has a spring-like resilience adapted to transmit a controlled compression force between the second outer race 210 and a portion of the housing end cap 35 adjacent the second bearing assembly 200 so as to provide axial pre-loading of the second bearing assemblies 200. The pre-load is transmitted from the second bearing assembly 200 to the first bearing assembly 100 through the rotor shaft 75.

In a preferred embodiment, the spacer ring 280 is a spring washer fabricated from stainless steel using conventional fabrication techniques. From this disclosure, it would be obvious to one of ordinary skill in the art that other types of resilient spacer rings (for example, a Belleville washer fabricated from other high strength metals or a flat washer fabricated from a material having suitable elastic properties) could be substituted. Also based on this disclosure, the person of ordinary skill in the art would further recognize that the relative proportions of the components illustrated could be varied without departing from the spirit and scope of the invention.

As noted above, a first problem associated with the prior art is providing a design which prevents an outer race of a bearing of a dental turbine motor from spinning during operation. In operation of the present invention, the pair of rings 170 provide increased force restraining rotational motion of the first outer race 110 over the force provided which would be provided by a single ring (as disclosed in Kerfoot, Jr.) and thus the pair of rings 170 prevents spinning of the first outer race 110 better than does a single ring. This result stems from the fact that frictional force between two bodies in contact is, to a very good first approximation, independent of the area of contact and only dependent upon the normal force between the contacting surfaces of the two bodies and the coefficient of friction (static or dynamic) at the surfaces. For a constant normal force, doubling the number of rings in contact with a surface doubles the frictional force resisting rotation of the surface relative to the rings. More specifically, in terms applicable to the present invention, the frictional force developed by the pair of resilient rings 170 engaged with the first outer wall 115 is a function of a normal force between an inner diameter of the each of the pair of rings 170 and the first outer wall 115 (the normal force resulting from stretching of the pair of rings 170 over the first outer wall 115) and a coefficient of friction between the material of the pair of rings 170 and the material of the first outer wall 115. The frictional force resisting rotation of the outer race 110 provided by the pair of rings 170 is thus twice that which would be provided by a single ring, assuming the same normal force.

As is further noted above, a second problem associated with the prior art is that a spring washer of a bearing assembly proximate a dental tool tends to deform and flatten with use. Applicant has noted that deflections imposed upon a spring washer of a bearing assembly distal to a dental tool are reduced, and thus positioning of the spacer ring 280 in the second bearing assembly 200 mitigates the second problem associated with the prior art. As is also noted above, providing a spacer ring only at a rear bearing is not disclosed by Kerfoot, Jr.

The preferred embodiment of the present invention discloses a pair of rings 170 located only at the first bearing assembly 100. From this disclosure, it would be obvious to one of ordinary skill in the art that the pair of rings 170 could also be used in the second bearing assembly 200 in place of the single ring 270.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention.

We claim:

1. A dental handpiece for rotating a dental workpiece, the dental handpiece comprising:
   a housing having a first end and a second end;
   a gas-driven turbine motor assembly including a rotor shaft having an axis of rotation substantially coincident with a central longitudinal axis of the housing;
   a chuck assembly secured to the rotor shaft, the chuck assembly releasably holding a shaft of the dental workpiece;
   a first bearing assembly radially supporting the motor assembly and disposed toward the first end of the housing and including:
   an inner race fixed to the rotor shaft;
   an outer race having an outer wall facing radially outwardly of the axis of the rotor shaft;

a plurality of movable bearing elements confined between the inner race and the outer race;

a first flange connected to a first end of the outer wall of the outer race, the first flange having a first lateral face disposed toward the first end of the housing and a second lateral face disposed toward the second end of the housing;

a first groove extending circumferentially about a second end of the outer wall of the outer race, the first groove lying in a plane substantially perpendicular to the axis of the rotor shaft;

a first snap ring retained within the first groove, the snap ring forming an annular-shaped collar extending radially outwardly of the outer race outer wall, the snap ring having first and second lateral faces, the first lateral face being oriented toward the first end of the housing and a portion of the first lateral face of the snap ring contacting a portion of the housing;

a first pair of resilient rings disposed between the second lateral face of the snap ring and the first lateral face of the flange and frictionally engaged with the outer wall of the outer race, each of the rings having an outer diameter sufficient to provide a compression fit between the outer wall of the outer race and the housing;

a second bearing assembly radially supporting the motor assembly and disposed toward the second end of the housing and including:

an inner race fixed to the rotor shaft, an outer race having an outer wall facing radially outwardly of the axis of the rotor shaft;

a plurality of movable bearing elements confined between the inner race and the outer race;

a second flange connected to a first end of the outer wall of the outer race of the second bearing assembly, the second flange having a first lateral face disposed toward the first end of the housing and a second lateral face disposed toward the second end of the housing;

a second groove extending circumferentially about a second end of the outer race outer wall of the second bearing assembly, the second groove lying in a plane substantially perpendicular to the axis of the rotor shaft;

a second snap ring retained within the second groove, the second snap ring forming an annular-shaped collar extending radially outwardly of the outer race outer wall of the second bearing assembly, the second snap ring having first and second lateral faces, the second lateral face being oriented toward the second end of the housing and a portion of the second lateral face of the second snap ring contacting the housing;

a single resilient ring disposed between the first lateral face of the second snap ring and the second lateral face of the second flange and frictionally engaged with the outer wall of the outer race of the second bearing assembly, the ring having an outer diameter sufficient to provide a compression fit between the outer race outer wall and the housing;

a substantially flat washer disposed between the ring and the second lateral face of the second flange;

a resilient spring-like spacer ring interposed between the second face of the second flange and the flat washer, the spacer ring transmitting a controlled compression force between the outer race of the second bearing assembly and the housing to provide axial pre-loading of the first and second bearing assemblies.

2. The dental handpiece of claim 1 wherein the resilient rings are O-rings fabricated of an elastomeric material such as Viton®.

3. The dental handpiece of claim 1 wherein the single resilient ring is replaced by a second pair of resilient rings.

4. The dental handpiece of claim 3 wherein the first pair of resilient rings is replaced by a single resilient ring.

5. The dental handpiece of claim 1 wherein the resilient spacer ring is a spring washer.

6. The dental handpiece of claim 1 wherein the pair of resilient rings are compressed in the direction of the rotor shaft to provide a static pre-load to the bearing assemblies when the turbine motor assembly is operably positioned within the housing.

* * * * *

UNITED STATES PATENT AND TRADEMARK OFFICE
CERTIFICATE OF CORRECTION

PATENT NO. : 6,790,039 B1
DATED : September 14, 2004
INVENTOR(S) : Stanley A. Brown It is certified that error appears in the above-identified patent and that said Letters Patent is hereby corrected as shown below:

Title page,
Item [73], Assignee, should read -- DentalEZ, Inc., Malvern, PA (US) --

Signed and Sealed this

Fourteenth Day of December, 2004

JON W. DUDAS
*Director of the United States Patent and Trademark Office*